(12) United States Patent
Jansen

(10) Patent No.: US 7,668,584 B2
(45) Date of Patent: Feb. 23, 2010

(54) INTERFACE APPARATUS FOR PASSIVE TRACKING SYSTEMS AND METHOD OF USE THEREOF

(75) Inventor: Herbert André Jansen, Montréal (CA)

(73) Assignee: Orthosoft Inc., Montréal (CA)

( * ) Notice: Subject to any disclaimer, the term of this patent is extended or adjusted under 35 U.S.C. 154(b) by 502 days.

(21) Appl. No.: 10/524,733

(22) PCT Filed: Aug. 11, 2003

(86) PCT No.: PCT/CA03/01217

§ 371 (c)(1),
(2), (4) Date: Feb. 16, 2005

(87) PCT Pub. No.: WO2004/016178

PCT Pub. Date: Feb. 26, 2004

(65) Prior Publication Data

US 2006/0173264 A1    Aug. 3, 2006

Related U.S. Application Data

(60) Provisional application No. 60/403,642, filed on Aug. 16, 2002.

(51) Int. Cl.
*A61B 5/05* (2006.01)
(52) U.S. Cl. ............ 600/424; 600/426; 600/427; 600/429; 702/95

(58) Field of Classification Search .......... 600/424, 600/429; 702/95
See application file for complete search history.

(56) References Cited

U.S. PATENT DOCUMENTS

| | | | | |
|---|---|---|---|---|
| 6,021,343 A | * | 2/2000 | Foley et al. | 600/429 |
| 6,061,644 A | * | 5/2000 | Leis | 702/153 |
| 6,529,765 B1 | * | 3/2003 | Franck et al. | 600/427 |

* cited by examiner

*Primary Examiner*—Long V Le
*Assistant Examiner*—Ellsworth Weatherby
(74) *Attorney, Agent, or Firm*—Ogilvy Renault LLP

(57) ABSTRACT

An interface apparatus (20) for tracking by a tracking system (40) of an object(s) in space for position and orientation and for interacting with the tracking system (40). The interface apparatus (30) comprises passive detectable devices (12,14, 16,22) trackable for position by the tracking system (40). A mounting device (10,24) receives the passive detectable devices (12,14,16,22) in a known geometry, and is secured to the object(s) such that a position and orientation of the object(s) is calculable by the tracking system (40) as a function of a tracking of the known geometry of the passive detectable devices (12,14,16,22). One of the passive detectable devices (22) is displaceable with respect to the object(s). A displacement of the passive detectable device (22) with respect to the object(s) is detectable to initiate an interaction with the tracking system (40) while maintaining the tracking of the object(s).

12 Claims, 2 Drawing Sheets

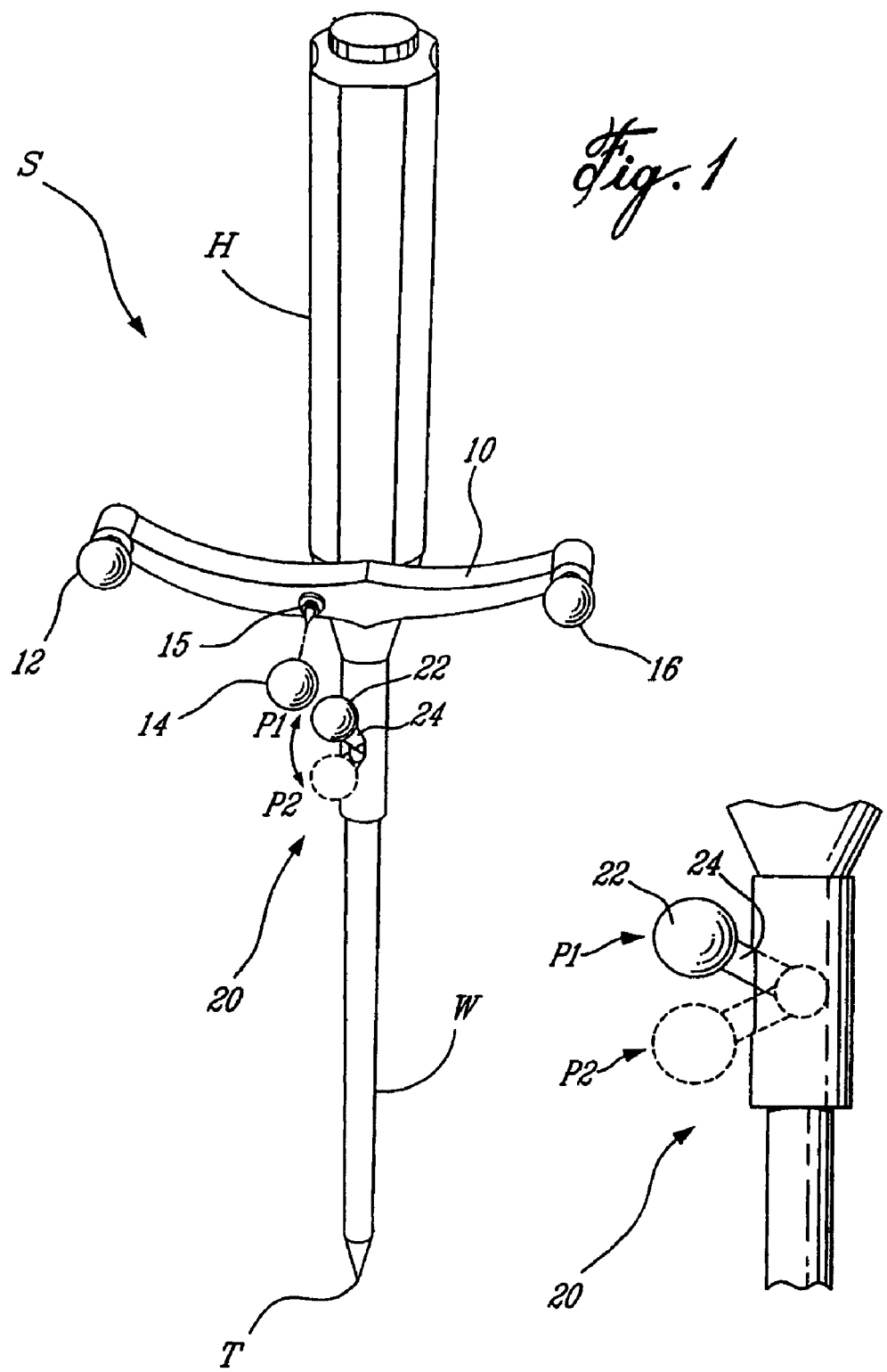

INTERFACE APPARATUS FOR PASSIVE TRACKING SYSTEMS AND METHOD OF USE THEREOF

CROSS-REFERENCE TO RELATED APPLICATION

This application is a national entry of International Patent Application No. PCT/CA2003/001217, filed on Aug. 11, 2003, and claims priority on U.S. Provisional Patent Application No. 60/403,642, filed on Aug. 16, 2002.

FIELD OF THE INVENTION

The present invention generally relates to optical tracking systems and, more particularly but not exclusively, to interaction between a tool operator and a tracking system.

BACKGROUND OF THE INVENTION

There are many advantages to being able to operate a computer-aided surgery (CAS) system in an operating room. For a system that allows real-time display of the relative positions of three-dimensional models of anatomical structures and of a surgical tool by tracking of the latter, this means being able to select a component or section of an image displayed on a monitor and perform operations on it such as zooming in and out, rotating it, etc. It also means enabling a surgeon to digitize points, whereby the latter may, for instance, define a profile of an operated bodily part.

The interaction between the surgeon and the CAS system presents some difficulties. For one thing, the surgeon operates in a sterile zone, whereas components of the CAS system are in a non-sterile zone. To perform some computer-related operations, such as controlling the monitor displays, the surgeon is required to interact with the CAS system. For instance, the act of selecting an object on a screen is typically done with a computer mouse, the mouse directing a visible cursor to the desired point on the image. However, due to the need for all objects in the sterile zone of the operating room to be sterile, a mouse cannot be used in the sterile zone to perform such actions.

In order to get around the fact that a mouse is not sterile, it is possible to have a person other than the surgeon interacting with the CAS system. In this case, the surgeon, or other person manipulating a surgical tool, needs to verbalize very specific instructions to the person interacting with the CAS system in order to obtain the desired results. This technique is both tedious and inefficient.

Since the field of interactive CAS systems is relatively new, there is no prior art that covers the concept of providing an interface within the sterile zone by which the surgeon may interact with the CAS system by way of a tracking system.

SUMMARY OF THE INVENTION

It is an object of the present invention to provide a sterile interface for interaction with CAS systems.

It is another object of the present invention to provide an interface for interaction with a CAS system as a function of a tracking of a tool.

Therefore, in accordance with the present invention, there is provided an interactive tracking system for tracking a position and orientation of a tool and for interaction with an operator of the tool in computer-assisted surgery, the interactive tracking system comprising a detectable device trackable for position and orientation and adapted to be mounted to a tool; an interaction device adapted to be mounted to the tool and actuatable to send an interaction signal relating to a function of the tool; a tracking system for tracking the detectable device for position and orientation; and a computer-assisted surgery system connected to the tracking system for calculating a position and orientation of the tool as a function of the tracking of the detectable device and for initiating an interaction as a function of the position and orientation of the tool when receiving the interaction signal.

Further in accordance with the present invention, there is provided a passive optical interface apparatus for tracking by a tracking system of an object in space for position and orientation and for interacting with the tracking system, the passive optical interface apparatus comprising at least three passive detectable devices trackable for position by the tracking system; and a mounting device for receiving the three passive detectable devices in a known geometry and adapted for being secured to the object such that a position and orientation of the object is calculable by the tracking system as a function of a tracking of the known geometry of the passive detectable devices, at least a first one of the passive detectable devices being displaceable with respect to the object, a displacement of said first one of the passive detectable devices with respect to the object being detectable to initiate an interaction with the tracking system while maintaining the tracking of the object.

Still further in accordance with the present invention, there is provided a method for interaction between a tracking system tracking a position and orientation of an object in space and a handler of the object, the object having at least one detectable device with at least two detectable configurations, comprising the steps of: i) tracking a position and orientation of the detectable device for calculating a position and orientation of the object as a function of the position and orientation of any one of the detectable configurations of the detectable device; ii) interpreting a change between the detectable configurations as an interaction signal from the handler; and iii) responding to the interaction signal by initiating an interaction response to the handler.

BRIEF DESCRIPTION OF THE DRAWINGS

These and other features, aspects and advantages of the present invention will become better understood with regard to the following description and accompanying drawings wherein:

FIG. 1 is a perspective view of a surgical instrument having a computer interface device in accordance with the present invention;

FIG. 2 is an enlarged fragmented side elevational view of the computer interface device;

DETAILED DESCRIPTION OF THE PREFERRED EMBODIMENT

Figure 3:
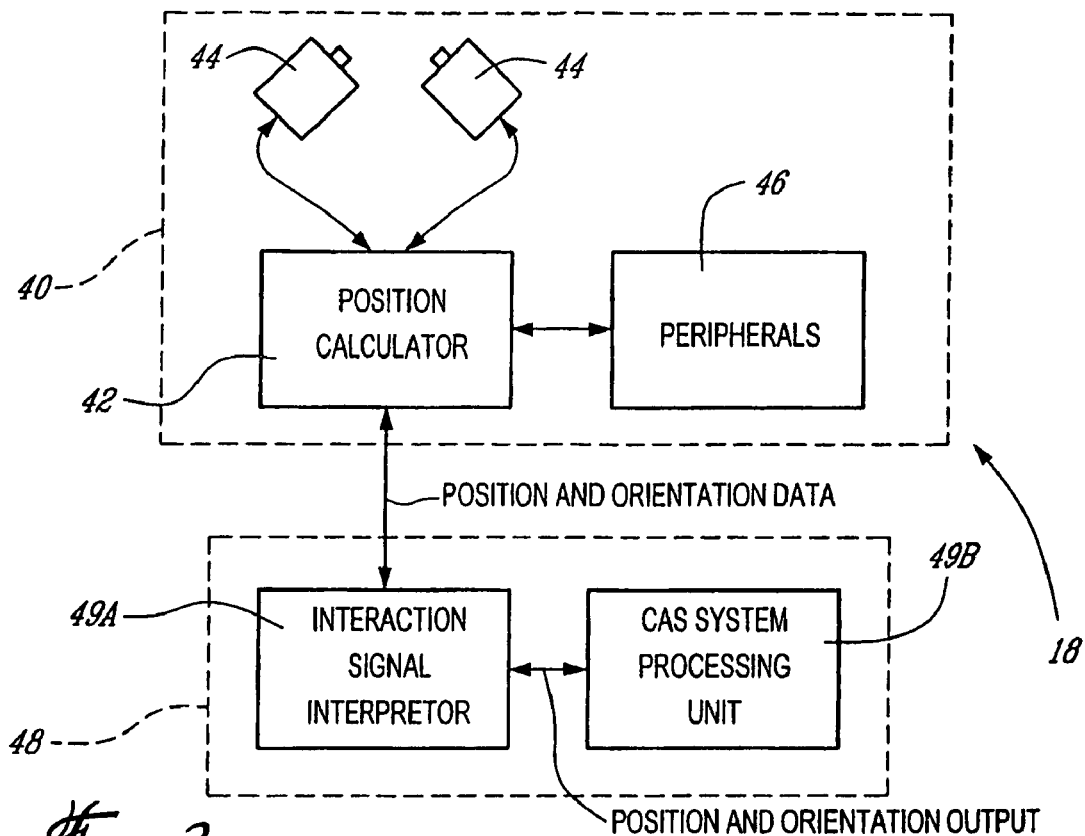
FIG. 3 is a schematic representation of an interactive tracking system in accordance with the present invention.

Referring now to FIG. 1, a tool is generally shown at S. It is pointed out that the tool S may take a plurality of forms. The tool S has a working tip T at an end of a working shaft W and a handle portion H. A blade 10 is secured to the tool S. More precisely, the blade 10 is positioned adjacent to the junction between the handle portion H and the working shaft W. The blade 10 comprises detectable spheres 12, 14 and 16. An interface apparatus is generally shown at 20 and is positioned at an end of the working shaft W adjacent to the handle portion H. It is pointed out that the interface apparatus 20 may be positioned elsewhere on the tool S, but is preferably within reach of the fingers of the surgeon. The interface apparatus 20 has a detectable sphere 22 which is mounted at an end of a lever 24. As shown in FIGS. 1 and 2, the lever 24 may move between a first position, as shown by P1, and a second position, as shown by P2. The lever 24 may be biased such that the detectable sphere 22 remains, for instance, at position P1. Accordingly, when the lever 24 is moved to P2, the lever 24 returns automatically to position P1.

The detectable spheres 12, 14, 16 and 22 are each coated with a retro-reflective layer in order to be detected by, for instance, an infrared sensor using axial illumination. It is pointed out that other shapes could be used as alternative embodiments to retro-reflective spheres. As an example, straight cylinders, corner reflectors or the like having retro-reflective properties could also be used. It is preferred that the detectable devices be passive, such that they are wireless. In surgical applications, having wires connecting a CAS to a surgical tool could create sterility issues, as the wires require to extend out of the sterile zone. It is obviously possible to use active detectable devices, such as wireless magnetic sensors.

The detectable sphere 14 is shown removed from the blade 10. The detectable spheres 12, 16 and 22 may also be removed from the tool S, as each sphere is snap-fitted to an adaptor. One such adaptor is shown at 15 in FIG. 1. Therefore, single-use sterilized spheres may be used, or other spheres which may be sterilized with processes milder than autoclave sterilization (which is typically used for sterilizing surgical tools and instruments), whereby a retro-reflective coating does not need to be characterized by its capability to sustain high temperatures or pressures. The tool S is preferably of materials adapted to be sterilized through an autoclave process.

The detectable spheres 12, 14 and 16 represent a geometrical pattern used for the tracking of the surgical tool S and will be referred to hereinafter as geometrical pattern 12-14-16. The detectable spheres 12, 14 and 16 are tracked by optical sensors of an interactive tracking system 18, which recognizes the pattern 12-14-16 and knows the relation of the pattern 12-14-16 with respect to the tool S. Therefore, the position and orientation of the tool are calculable as a function of the tracking of the pattern 12-14-16. The detectable spheres 12, 14 and 16 thus allow for all six degrees of freedom of the surgical tool S to be known when the surgical tool S is displaced in the working range of the interactive tracking system 18.

In a first embodiment of the present invention, the detectable sphere 22 is used with two of the three spheres on the blade 10 in order to make another optically detectable geometrical pattern. For instance, detectable spheres 12, 14 and 22 form a geometrical pattern (hereinafter referred to as pattern 12-14-P1) when the detectable 12-14-P1 is tracked for position and orientation simultaneously with the tracking of the geometrical pattern 12-14-16. As the tool S and all detectable spheres thereon are tracked for position and orientation, a move of the detectable sphere 22 from position P1 to position P2 will modify the optical pattern 12-14-P1, and this will be detected by the interactive tracking system 18. The modification detected by the interactive tracking system 18 will be interpreted as an interaction signal thereby. Accordingly, the tool operator is enabled to send a signal to the interactive tracking system 18 by flicking the lever 24 out of position P1, and this is equivalent to a "click" of a mouse button. It is also possible to use a third pattern, with the detectable sphere 22 held in position P2, and referred to as pattern 12-14-P2. The two patterns, 12-14-P1 and 12-14-P2, enable the operator to use a time dimension (as opposed to a click). For instance, pattern 12-14-P1 may represent an OFF position, while pattern 12-14-P2 represents an ON position. Therefore, this ON/OFF switching may be linked to various functions in the CAS system. It is pointed out that the optical patterns 12-14-16, 12-14-P1 and 12-14-P2 must each be different from one another. Furthermore, all patterns defined by the detectable sphere 22 moving from P1 to P2 must not be similar to the pattern 12-14-16, in order for the sensor not to confuse the patterns one for another.

In a second embodiment of the present invention, a vector is defined between the detectable sphere 22 at one position and one of the detectable spheres 12, 14 and 16. For instance, having detectable sphere 12 as the reference point, a vector is defined between the detectable sphere 22 at position P1 and the detectable sphere 12, and is referred to as vector 12-P1. A modification of the vector 12-P1 by a displacement of the detectable sphere 22 is detected by the interactive tracking system 18 of the CAS system, which will then send a signal to the CAS system. It is pointed out that a vector 12-P2 (i.e., with the detectable sphere at position P2) may be used as a second position and orientation, similar to the ON/OFF switching described above.

The interactive tracking system 18 is typically an optical tracking system capable of tracking the real-time position and orientation of at least three detectable devices in a working space. However, although the preferred embodiments of the present invention incorporate passive detectable devices (i.e., the detectable spheres 12, 14, 16 and 22), the tracking system 18 may be an active tracking system. Referring to FIG. 3, the various components of the interactive tracking system 18 are schematically shown. The interactive tracking system 18 is mainly composed of a tracking system 40 and a CAS system 48 in operative relation therewith. The CAS system 48 has an interaction signal interpreter 49A and a CAS system processing unit 49B. The tracking system 40 consists of a position calculator 42 connected to sensors 44 to track detectable devices on a tool or object for position and orientation. The position calculator 42 is typically connected to peripheral 46, such as a monitor, a keyboard and a mouse. The interaction signal interpreter 49A of the CAS system 48 is programmed to detect the interaction signals, e.g., as set forth in the first and second embodiments of the present invention, such that the interactive tracking system 18 may initiate an interaction with the tool operator, or object handler. The interaction between the interactive tracking system 18 and the tool operator can be a function of the position and orientation of the tool being tracked. For instance, zooming actions may take place on the monitor of the peripherals 46. The tool can be a pointer, whereby points in space may be digitized using the interaction signals to indicate points (e.g., registration of a bone by a pointer in CAS). A menu may be presented to a tool operator on a monitor of the peripherals 46.

The interaction signal interpreter 49A filters the position and orientation data from the position calculator 42, and forwards the position and orientation data to the CAS system processing unit 49B, for the tracking of a tool or object. The interaction signal interpreter 49A will detect an interaction signal from the position and orientation data received from the position calculator 42.

As mentioned previously, it is preferred that the tracking system 40 be an optical tracking system, to operate the interactive tracking system 18 with the interface apparatus 20 described above. However, the correlation between the tracking of an object for position and orientation, and the interaction between the interactive tracking system 18 and the object handler/tool operator is a feature of the present invention that is not to be limited to the use of passive tracking. When an optical tracking system 40 is used, the Polaris® Optical Tracking System by Northern Digital Inc. is suitable for such purposes. It is pointed out that the detectable spheres 12, 14, 16 and 22 must be positioned on the tool S in compliance with the requirements of the interactive tracking system 18. For example, the Polaris® Optical Tracking System requires that the detectable spheres are separated from one another by at least 5 cm. It is also a requirement for this tracking system that each segment between detectable spheres must differ from the other segments by at least 5 mm.

Figure 4:
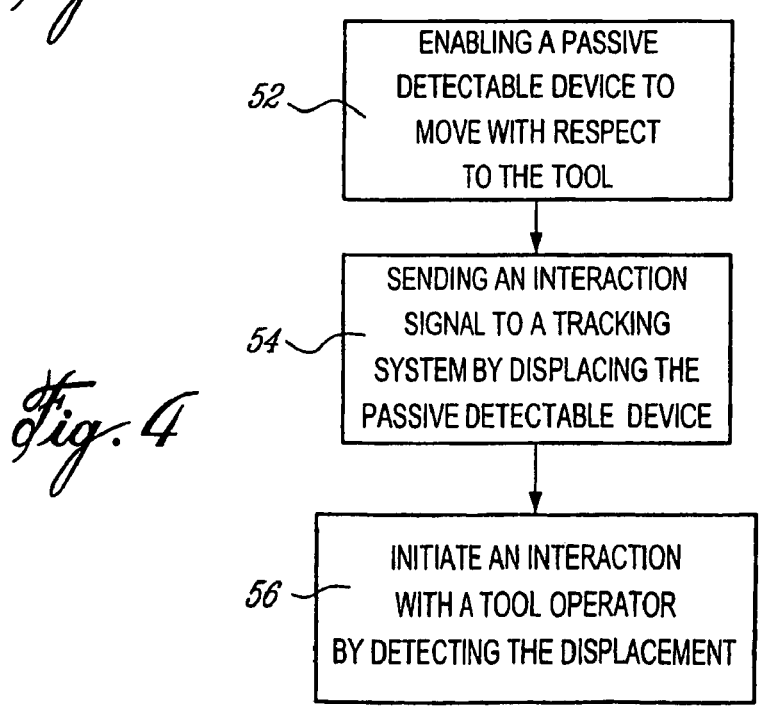
FIG. 4 is a block diagram illustrating a method for interaction between the interactive tracking system and a tool operator, in accordance with the present invention.

Referring to FIG. 4, the actions on the interactive tracking system 18 and the interface apparatus 20 are illustrated at 50. According to step 52, a detectable device secured to an object in a detectable configuration is tracked for position and orientation. According to step 53, a position and orientation of the object is be calculated as a function of the tracking of the detectable device. According to step 54, a change in detectable configuration is interpreted as an interaction signal. Step 52 is independent from step 54 and is continuous, whereby the detectable device is tracked for position and orientation for any detectable configuration thereof and is not interrupted by step 54. According to step 56, an interaction response is initiated to respond to the interaction signal of step 54. The interaction response may be a function of the position and orientation of the object.

The above-described interface apparatus 20 may be used with other typical elements of the CAS system, such as, for instance, a calibration base having detectable spheres configured similarly to the above-described embodiments. The signal of a movable sphere detected by the sensor 18 may be used for the CAS system to take a calibration reading.

Having the interface apparatus 20 on the surgical tool S is advantageous, as the surgeon is no longer required to move out of his sterilized zone in order to interact with the CAS system. It is pointed out that the detectable sphere 22 is not restricted to two positions and, therefore, a plurality of various positions may allow the tool operator to interface with the computer in many various ways.

Also, the present invention is not restricted to using lever 24 as the interface device 22. A switch sliding between positions, an indexed disk, a push button or the like may be used as long as a detectable element is displaceable on the surgical tool S between at least first and second positions and orientations. Although the use of four detectable spheres, one of which is moveable, is preferred, other ways of providing a signal detectable by the interaction signal interpreter 48 are considered. For instance, a mechanism can be provided that would enable a precise and detectable motion of a pattern of the detectable spheres with respect to the tool, such as a quick tilt. There is however a risk that the given motion be inadvertently executed by an operator. Also, two active sensors can be provided onto the tool, with one of the sensors being displaceable with respect to the tool while the other one is immovable with respect to the tool. A relative displacement between the active sensors can thereafter be used to initiate an interaction signal between a CAS system and a surgeon, with the immovable active sensor being continuously tracked for position and orientation so as to have a continuous tracking of the tool.

The invention claimed is:

1. A passive optical interference apparatus for tracking by a tracking system of an object in space for position and orientation and for interacting with the tracking system, the passive optical interface apparatus comprising:

at least three passive detectable devices trackable for position by the tracking system; and a mounting device for receiving the at least three passive detectable devices in a known geometry and adapted for being secured to the object such that a position and orientation of the object is calculable by the tracking system as a function of a tracking of the known geometry of the at least three passive detectable devices, at least a first of the at least three passive detectable devices being secured to the mounting device by a pivot joint, the pivot joint operatively connecting said first of the at least three passive detectable devices for pivotal movement between a first position and a second position with respect to the object, a pivotal displacement of said first of the at least three passive detectable devices to any one of said first position and said second position with respect to the object being detectable to initiate an interaction with the tracking system while maintaining the tracking of the object.

2. The passive optical interface apparatus according to claim 1, wherein the apparatus comprises four of said passive detectable devices trackable for position by the tracking system, a second, a third and a fourth of the four passive detectable devices being positioned in said known geometry and the first of the four passive detectable devices being displaceable with respect to the known geometry, a displacement of the first of the four passive detectable devices with respect to the known geometry being detectable to initiate an interaction with the tracking system.

3. The passive optical interface apparatus according to claim 2, wherein the first of the four passive detectable devices is displaceable between said first position and said second position with respect to the known geometry, a displacement of the first of the four passive detectable devices from the first position to the second position being interpreted by the tracking system as a first type of interaction, a displacement of the first of the four passive detectable devices from the second position to the first position being interpreted by the tracking system as a second type of interaction.

4. The passive optical interface apparatus according to claim 2, wherein the first of the four passive detectable devices is biased to said first position by the mounting device, a displacement of the first of the four passive detectable devices away from the first position being detectable to initiate an interaction with the tracking system.

5. A method for interaction between a tracking system tracking a position and orientation of an object in space and a handler of the object, the object having at least three passive detectable devices with at least one of said at least three passive detectable devices being pivotally displaceable with respect to the object so as to define at least two detectable geometrical patterns and, comprising:

i) tracking a position and orientation of the at least three passive detectable devices for calculating a position and orientation of the object as a function of the position and orientation of any one of the detectable geometrical patterns of at least three passive detectable devices;

ii) interpreting a pivotal displacement of said at least one of said at least three passive detectable devices with respect to the object as an interaction signal from the handler; and iii) responding to the interaction signal by initiating an interaction response to the handler, the interaction response being unrelated to a variation of the position and orientation of the object.

6. The method according to claim 5, wherein the change is a displacement of a first of the passive detectable devices between a first position and a second position, the detectable device having four of the passive detectable devices, with the first geometrical pattern being a second, a third and a fourth of the passive detectable devices in a known geometry and the first of the passive detectable devices in the first position with respect to the known geometry, and with the second geometrical pattern being the second, the third and the fourth of the passive detectable devices in the known geometry and the first of the passive detectable devices being in the second position with respect to the known geometry, the known geometry being fixed to the object such that the position and orientation of the object is calculated as a function of the position and orientation of the known geometry.

7. The method according to claim 5, wherein the change from a first to a second of the detectable configurations is interpreted in step ii) as a first type of the interaction signal, and the change from the second to the first of the detectable configurations is interpreted in step ii) as a second type of the interaction signal.

8. The method according to claim 7, wherein a first type of the interaction signal is initiated in response to the first type of the interaction signal in step iii), and a second type of the interaction signal is initiated in response to the second type of the interaction signal in step iii).

9. The method according to claim 5, wherein the interaction response is a function of the position and orientation of the object.

10. An interaction signal interpreter computer program product comprising code means recorded in a computer readable memory for executing a method for interaction between a tracking system tracking a position and orientation of an object in space and a handler of the object, the object having at least three passive detectable devices with at least one of said at least three passive detectable devices being pivotally displaceable with respect to the object so as to define at least two detectable geometrical patterns and, comprising the steps of tracking a position and orientation of the at least three passive detectable devices for calculating a position and orientation of the object as a function of the position and orientation of any one of the detectable geometrical patterns of at least three passive detectable devices; interpreting a pivotal displacement of said at least one of said at least three passive detectable devices with respect to the object as an interaction signal from the handler; and responding to the interaction signal by initiating an interaction response to the handler, the interaction response being unrelated to a variation of the position and orientation of the object.

11. The method according to claim 5, wherein the change is a displacement of a first of the passive detectable devices away from a first position, the detectable device having four of the passive detectable devices, with the first geometrical pattern being a second, a third and a fourth of the passive detectable devices in a known geometry and the first of the passive detectable devices in the first position with respect to the known geometry, and with the second geometrical pattern being the second, the third and the fourth of the passive detectable devices in the known geometry and the first of the passive detectable devices being away from the first position with respect to the known geometry, the known geometry being fixed to the object such that the position and orientation of the object is calculated as a function of the position and orientation of the known geometry.

12. A passive optical interface apparatus for tracking by a tracking system of an object in space for position and orientation and for interacting with the tracking system, the passive optical interface apparatus comprising:

at least three passive detectable devices trackable for position by the tracking system; and a mounting device for receiving the at least three passive detectable devices in a known geometry and adapted for being secured to the object such that a position and orientation of the object is calculable by the tracking system as a function of a tracking of the known geometry of the at least three passive detectable devices, at least a first of the at least three passive detectable devices being secured to the mounting device by a pivot joint and biased to an position with respect to the object by a biasing means, the pivot joint allowing a displacement of said at least a first of the at least three passive detectable away from said position with respect to the object, said displacement being detectable to initiate an interaction with the tracking system while maintaining the tracking of the object.

* * * * *